United States Patent [19]

Sando et al.

[11] Patent Number: 4,656,843
[45] Date of Patent: Apr. 14, 1987

[54] APPARATUS FOR THE AUTOMATIC CONCENTRATION CONTROL OF AQUEOUS CAUSTIC SODA SOLUTION

[75] Inventors: Yoshikazu Sando; Hiroshi Ishidoshiro, both of Wakayama, Japan

[73] Assignee: Sando Iron Works Co., Ltd., Wakayama, Japan

[21] Appl. No.: 672,794

[22] Filed: Nov. 19, 1984

[30] Foreign Application Priority Data

Nov. 21, 1983 [JP] Japan ................................. 58-218892

[51] Int. Cl.$^4$ .............................................. D06B 3/10
[52] U.S. Cl. ................................................... 68/13 R
[58] Field of Search ...................... 68/12 R, 13 R, 207

[56] References Cited

U.S. PATENT DOCUMENTS 3,496,740  2/1970  Borochaner .......................... 68/12 R
3,772,901 11/1973  Ferraro ................................ 8/158 X
3,841,116 10/1974  Klein et al. .......................... 68/12 R Primary Examiner—Philip R. Coe
Assistant Examiner—Frankie L. Stinson
Attorney, Agent, or Firm—Toren, McGeady & Goldberg

[57] ABSTRACT

An apparatus for the automatic concentration control of an aqueous caustic soda solution in a cloth treating tank through which a cloth to be treated is continuously transported, comprising the provision of a means for adding a neutralization agent to a sample of the caustic soda solution which was squeezed out of a cloth that had been soaked with an aqueous caustic soda solution while in a cloth treating tank; a sensor for detecting the neutralization point of said caustic soda sample solution, to which the neutralization agent is added on the basis of electrical conductivity; a means for detecting the caustic soda concentration of said caustic soda sample solution prior to the addition of the neutralization agent on the basis of the amount of the neutralization agent added until said caustic soda sample solution becomes neutralized as detected by means of said sensor; and a means for supplying a supplementary caustic soda solution to the caustic soda solution in said cloth treating tank so that its concentration is controlled to a prescribed value on the basis of the caustic soda concentration of the caustic soda sample solution detected by said detection means.

1 Claim, 1 Drawing Figure

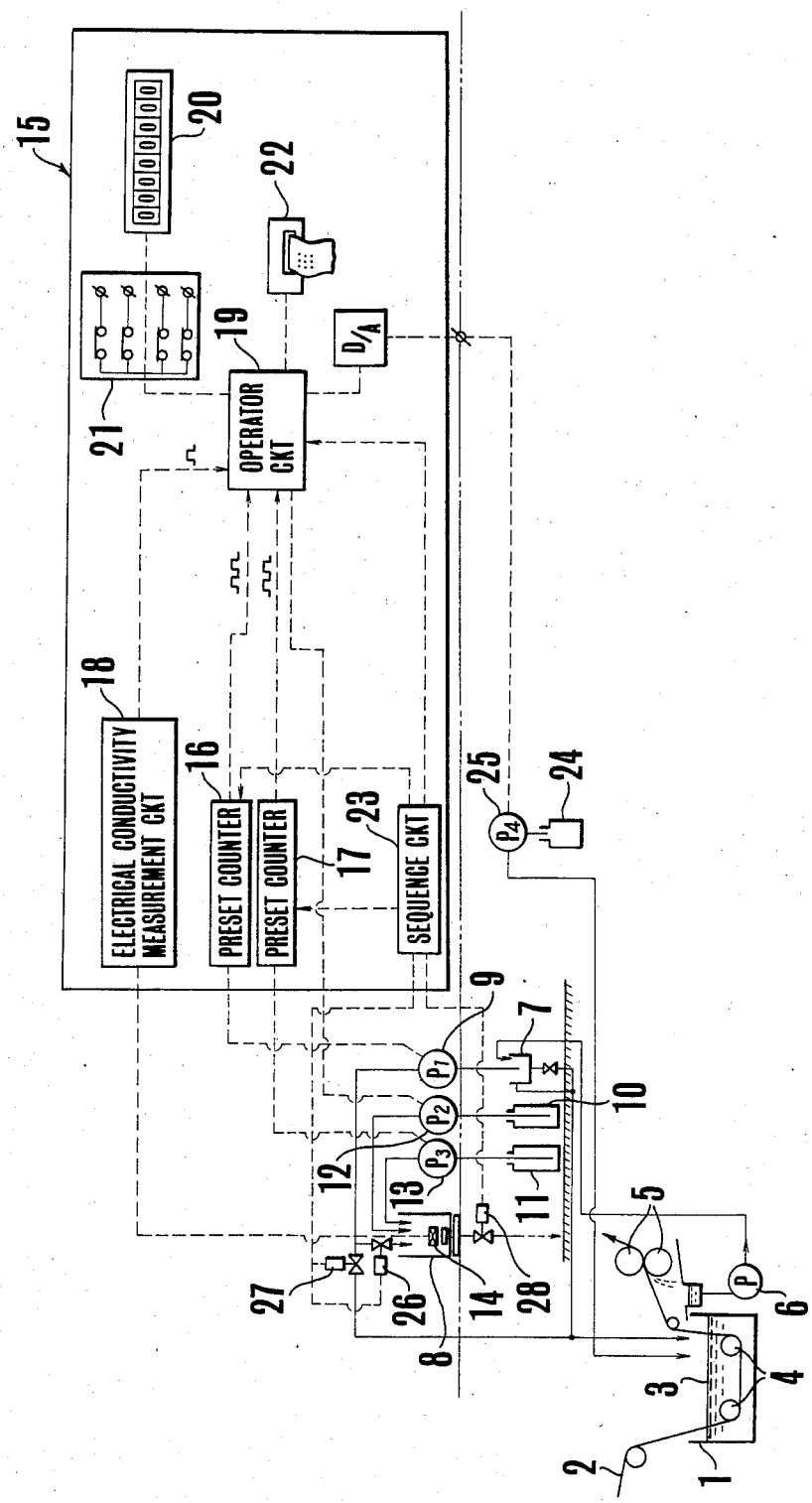

APPARATUS FOR THE AUTOMATIC CONCENTRATION CONTROL OF AQUEOUS CAUSTIC SODA SOLUTION

BACKGROUND OF THE INVENTION

1. Field of the Invention

The present invention relates to an apparatus for the automatic concentration control of an aqueous caustic soda solution which is used in the continuous treatment of a long cloth.

2. Description of the Prior Art

In subjecting a long, commercially produced cloth to such treatments as pretreatment, weight reduction and mercerization continuously, it is common to soak the cloth to be treated with an aqueous caustic soda solution having a prescribed concentration in a cloth treating tank and then to subject the resultant cloth to treatments such as, heat and tension treatments. In such a treatment with the use of a caustic soda solution, however, a drawback exists such that the quality of the treated product becomes uneven due to the fact that the concentration of the caustic soda solution changes frequently during the course of treatment.

Therefore, it is necessary in such a continuous treatment of a cloth, to apply a caustic soda solution having a definite concentration. However, in transporting a long cloth continuously through a cloth treating tank containing a treating solution, the concentration of the caustic soda solution unavoidably becomes lower with time. Conventionally, therefore, the caustic soda concentration in the treating solution tank is determined manually at prescribed time intervals, and a supplementary caustic soda solution is supplied into the cloth treating tank based on the result of the determination of the controlled concentration of the caustic soda solution in the cloth treating tank. However, with such a manual operation, problems arise; one being that a skilled operator is needed and another being that a long time is necessary until the solution control is completed thus deteriorating the operation efficiency.

SUMMARY OF THE INVENTION

Under such circumstances, the object of the present invention is to offer an apparatus for the automatic concentration control of an aqueous caustic soda solution in a process for soaking a long cloth continuously with a caustic soda solution in a cloth treating tank.

The essential points of the present apparatus comprises a means for adding a neutralization agent to a sample of the caustic soda solution squeezed out of a cloth having been soaked with an aqueous caustic soda solution in a cloth treating tank; a sensor for detecting the neutralization point of said caustic soda sample solution, to which the neutralization agent is added, on the basis of electrical conductivity; a means for detecting the caustic soda concentration of said caustic soda sample solution prior to the addition of the neutralization agent on the basis of the amount of the neutralization agent added until said caustic soda sample solution becomes neutralized, as detected by means of said sensor; and a means for supplying a supplementary caustic soda solution to the caustic soda solution in said cloth treating tank so that its concentration is controlled to a prescribed value on the basis of the caustic soda concentration of the caustic soda sample solution detected by said detection means.

BRIEF EXPLANATION OF THE DRAWING

The drawing is an explanatory drawing showing an example of the present apparatus for the automatic concentration control of an aqueous caustic soda solution.

DETAILED DESCRIPTION OF THE INVENTION

The present invention will be described in detail in the following with reference to the drawing showing an example of the apparatus.

In the drawing, 1 is a cloth treating tank containing an aqueous caustic soda solution 3, to be applied to a cloth 2 which is transported continuously therethrough, and guide rollers 4 are provided in this solution tank 1 for immersing the cloth 2 into the solution. 5 is a pair of squeeze rollers for squeezing the excess of caustic soda solution out from the cloth 2 after being taken out of the solution tank 1. It is designed such that a portion of the aqueous caustic soda solution squeezed out from the cloth by means of the squeeze rollers 5 is sent to a sample solution collection container 7 by means of a pump 6, and the other portion thereof is returned to the cloth treating tank 1. 8 is a sample solution stirring container into which the caustic soda solution in the sample solution collection container 7 is transported, by means of a quantitative pulse pump 9. 10 is a dilution water tank, and 11 is neutralization agent solution tank in which for example, a sulfuric acid solution is introduced. It is designed such that the dilution water in the water tank 10 and the neutralization agent solution in the neutralization solution tank 11 are supplied quantitatively into the sample solution stirring container, 8 respectively, by means of quantitative pulse pumps 12 and 13. 14 is a concentration sensor immersed in the solution in said sample solution stirring container 8. The characteristic property of the electrical conductivity being lowered extremely at the neutralization point is utilized for the concentration sensor 14.

15 represents a solution concentration control unit comprising; preset counters 16 and 17 for detecting the amounts of the caustic soda solution and the neutralization agent solution supplied into the sample solution stirring container 8 by means of the quantitative pulse pumps 9 and 13, an electrical conductivity measurement circuit 18 by which the point at which the electrical conductivity in the concentration sensor 14 reaches its minimum is detected, an operation circuit 19 by which the caustic soda concentration of the caustic soda sample solution in the sample solution stirring container 8 is calculated on the basis of the signals from the measurement circuit 18 and the preset counters 16 and 17, a digital indicator 20 or a level indicator 21 by which the caustic soda concentration of the caustic soda sample solution is calculated through the use of the said operation circuit 19 is indicated by a radiation means, a printer 22 for printing out said indicated values, and a sequence circuit 23.

24 is a storage tank of a supplementary caustic soda solution, and it is designed in such a way that the caustic soda solution in the storage tank 24 is supplied into the cloth treating tank 1 by means of a quantitative pulse pump 25 operating on the basis of the signal from said operation circuit 19 so that the caustic soda concentration of the caustic soda solution in said cloth treating tank 1 becomes constant, at the prescribed value. 26, 27 and 28 are electromagnetic valves operated by the control signal from the sequence circuit 23. Due to the opening and closing movements of these electromagnetic valves, the supply and discharge of the sample solution into the sample solution stirring container 8 and the circulation of the sample solution in the sample solution collection container 7 are controlled so as to minimize the time lag between the caustic soda solution in the cloth treating tank 1 and the sample solution in the sample solution stirring container 8.

The construction of an example of the present apparatus is as above described. The automatic concentration control of an aqueous caustic soda solution in the cloth treating tank by using this apparatus will now be illustrated in the following.

In the process for soaking a cloth 2 to be treated with a caustic soda solution 3 in a cloth treating tank 1, the caustic soda concentration of said caustic soda solution is maintained at a constant level by the following procedure. First, a portion of the caustic soda solution squeezed out of the cloth that was soaked with the caustic soda solution through the use of a pair of squeeze rollers 5 is introduced by means of the pump 6 into the sample solution collection container 7, as a sample thereof while the remainder of said caustic soda solution is returned to the cloth treating tank 1. Then, said sample solution is introduced by driving the quantitative pulse pump 9 into the sample solution stirring container 8, and the amount of the sample solution introduced into the sample solution stirring container 8, in this instance, is counted by means of the preset counter 16 of the solution control unit 15. Next, by driving the quantitative pulse pump 12, the sample solution in the sample solution stirring container 8 is diluted with water from the dilution water tank 10 to a prescribed magnification while the resultant solution is stirred. In this instance, the additional amount of water for dilution, i.e., the operated amount from the quantitative pulse pump 12, is controlled by means of the signal from the solution control unit 15. (The object for dilution of the sample solution is to save the additional amount of the neutralization agent as will be mentioned hereafter.) Meanwhile, the neutralization agent solution (for instance, sulfuric acid solution) in the neutralization solution tank 11 is added drop by drop into the sample solution in the sample solution stirring container 8 by operating the quantitative pulse pump 13. When the sample solution is neutralized, the electrical conductivity value in the concentration sensor 14 in the sample solution stirring container 8 indicates a minimum value. It is then detected by means of the measurement circuit 18 that the sample solution reaches the neutralization point, and the additional amount of the neutralization agent added until the sample solution is neutralized, is detected by means of the operation circuit 19. Furthermore, in this instance, from the additional amount of the neutralization agent, the caustic soda concentration of the sample solution in the sample solution stirring container 8 is detected by means of the operation circuit 19, and the value of caustic soda concentration is indicated by means of the digital indicator 20 or the level indicator 21. Therefore, the caustic soda concentration of the sample solution can be ascertained by means of the indicators 20 or 21. It is advisable to provide one or more of said indicators at positions in the factory which are easily accessible for the control of said levels of concentration.

When the caustic soda concentration of the sample solution is indicated in this way, the quantitative pulse pump 25 is operated for supplying a definite amount of the caustic soda solution in the supplementary caustic soda solution storage tank 24, calculated by the operation circuit 19, into the aqueous caustic soda solution 3 in the cloth treating tank 1 so that the caustic soda solution in the cloth treating tank 1 can be controlled constantly to a prescribed caustic soda concentration.

As described in detail in the above, by using the present apparatus, the concentration of the caustic soda sample solution is indicated automatically, and accordingly, the caustic soda concentration of the caustic soda solution for the immersion of the cloth into the treating solution tank can be controlled automatically and constantly to the prescribed value. Therefore, there is no need for an operator for the solution control as in the conventional manually operated process, and the concentration control of the caustic soda solution can be done automatically at definite intervals. Moreover, according to the present invention, the sample solution is neutralized after the solution is diluted, so that the amount of the neutralization agent can economically be saved.

What is claimed is:

1. An apparatus for the automatic concentration control of an aqueous caustic soda solution in a cloth treating tank through which a cloth to be treated is continuously transported, comprising:

(i) a pair of squeeze rollers for squeezing a part of the soda solution out of a cloth that has been soaked with an aqueous caustic soda solution in a cloth treating tank;

(ii) means for introducing a portion of said caustic soda solution squeezed out of the cloth taken as a sample thereof in a sample solution stirring container while returning the remainder of said caustic soda solution to the cloth treating tank;

(iii) means for adding a neutralization agent to said caustic soda solution in said sample solution stirring container;

(iv) a sensor for detecting the neutralization point of said caustic soda sample solution in said sample solution stirring container while adding the neutralization agent thereof on the basis of electrical conductivity;

(v) means for detecting the original caustic soda concentration of said caustic soda sample solution after the addition of the neutralization agent on the basis of the amount of the neutrilization agent added until said caustic soda sample solution becomes neutralized, as detected by means of said sensor; and (vi) means for supplying a supplementary caustic soda solution to the caustic soda solution in said cloth treating tank for controlling the concentration of said caustic soda solution to a prescribed value on the basis of the caustic soda concentration of the caustic soda sample solution detected by said detection means.

* * * * *